(12) United States Patent
Culbert

(10) Patent No.: US 7,140,749 B2
(45) Date of Patent: Nov. 28, 2006

(54) RECESSED LAMP MOUNT

(75) Inventor: Robert Culbert, Manhattan Beach, CA (US)

(73) Assignee: Steril-Aire, Inc., Burbank, CA (US)

( * ) Notice: Subject to any disclaimer, the term of this patent is extended or adjusted under 35 U.S.C. 154(b) by 175 days.

(21) Appl. No.: 10/898,433

(22) Filed: Jul. 23, 2004

(65) Prior Publication Data

US 2006/0018115 A1 Jan. 26, 2006

(51) Int. Cl.
*F21S 4/00* (2006.01)
*B32B 5/02* (2006.01)
*B01J 19/08* (2006.01)
*G01N 23/00* (2006.01)

(52) U.S. Cl. .................. 362/217; 422/121; 422/186.3; 250/455.11

(58) Field of Classification Search ............... 362/217, 362/267; 422/121, 186, 186.3; 62/264; 250/455.11, 522.1
See application file for complete search history.

(56) References Cited

U.S. PATENT DOCUMENTS

| | | | |
|---|---|---|---|
| 4,637,223 A * | 1/1987 | Hosoya et al. ................ 62/263 |
| 4,990,313 A | 2/1991 | Pacosz | |
| 5,523,057 A * | 6/1996 | Mazzilli ..................... 422/121 |
| 5,755,103 A | 5/1998 | Na | |
| 5,866,076 A * | 2/1999 | Fencl et al. ................. 422/121 |
| 5,902,552 A | 5/1999 | Brickley | |
| 5,924,300 A * | 7/1999 | Fromm et al. ............. 62/259.1 |
| 6,193,939 B1 * | 2/2001 | Kozlowski ............... 422/186.3 |
| 6,221,314 B1 | 4/2001 | Bigelow | |
| 6,280,686 B1 | 8/2001 | Scheir | |
| 6,372,186 B1 * | 4/2002 | Fencl et al. ................. 422/121 |
| 6,589,486 B1 * | 7/2003 | Spanton ..................... 422/121 |
| 6,602,425 B1 * | 8/2003 | Gadgil et al. ............... 210/744 |
| 6,782,707 B1 * | 8/2004 | Shindo et al. ................ 62/264 |
| 2002/0174674 A1 * | 11/2002 | Takahashi et al. ........... 62/264 |
| 2003/0000229 A1 * | 1/2003 | Underwood ................... 62/78 |
| 2004/0208798 A1 * | 10/2004 | Splane et al. ............... 422/121 |

OTHER PUBLICATIONS

Ductwork gets a UV-Rx, curing mold growth problems; The Air Conditioning, Heating and Refrigeration NEWS; Aug. 11, 1997, 1 page, Business News Publishing Co.

* cited by examiner

*Primary Examiner*—Renee Luebke
*Assistant Examiner*—Evan Dzierzynski
(74) *Attorney, Agent, or Firm*—SoCal IP Law Group LLP; Steven C. Sereboff; Joel G. Landau

(57) ABSTRACT

There is disclosed a recessed cantilever mount and an installation process. The mount may comprise a cradle adapted to attach to a wall of a chassis and extend through an opening of the wall into the chassis, a retainer adapted to attach to the cradle and secure a stem of an electric discharge device to the cradle, wherein the stem is at least partially recessed in the cradle, and a tube of the electric discharge device is recessed within the chassis. The process may comprise recessing a base of a cradle through an opening in a wall of a chassis of an air handler selected from the group comprising a PTAC and a unit ventilator, securing the cradle to the wall, inserting a tube of an electric discharge device through an opening of the base into the chassis, and securing a rim of the electric discharge device against the base.

42 Claims, 7 Drawing Sheets

RECESSED LAMP MOUNT

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure as it appears in the Patent and Trademark Office patent files or records, but otherwise reserves all copyright and trade dress rights whatsoever.

BACKGROUND OF THE INVENTION

1. Field of the Invention

The present invention relates to recessed lamp mounts.

2. Description of the Related Art

Many homes, offices, and automobiles have recessed lighting systems. A recessed lighting system is an electrically powered lamp which is mounted in a fixture that is set back and concealed in a building's ceiling or wall. In general, the lamp of a recessed lighting system is housed within the recessed fixture. Typically, the lamp illuminates an area outside the ceiling, wall, or body panel, such as a living room or a kitchen.

Recessed fixtures are commonly used for aesthetic purposes, for example, to hide housings, sockets, wiring, ballasts, and switches. Recessed fixtures, in comparison with floor and/or table fixtures, enable space saving and clutter reduction. Recessed lighting is commonly configured to provide wall washing and accent lighting effects.

Recessed fixtures are commonly used for health and safety purposes. Recessed fixtures are often selected to promote ergonomics and create a well-lit work environment. In homes and offices, placing lamps and electric wires in the ceiling and/or wall prevents individuals from tripping on the wires.

DETAILED DESCRIPTION OF THE INVENTION

Throughout this description, the embodiments and examples shown should be considered as exemplars, rather than limitations on the apparatus and methods of the present invention.

Figure 1:
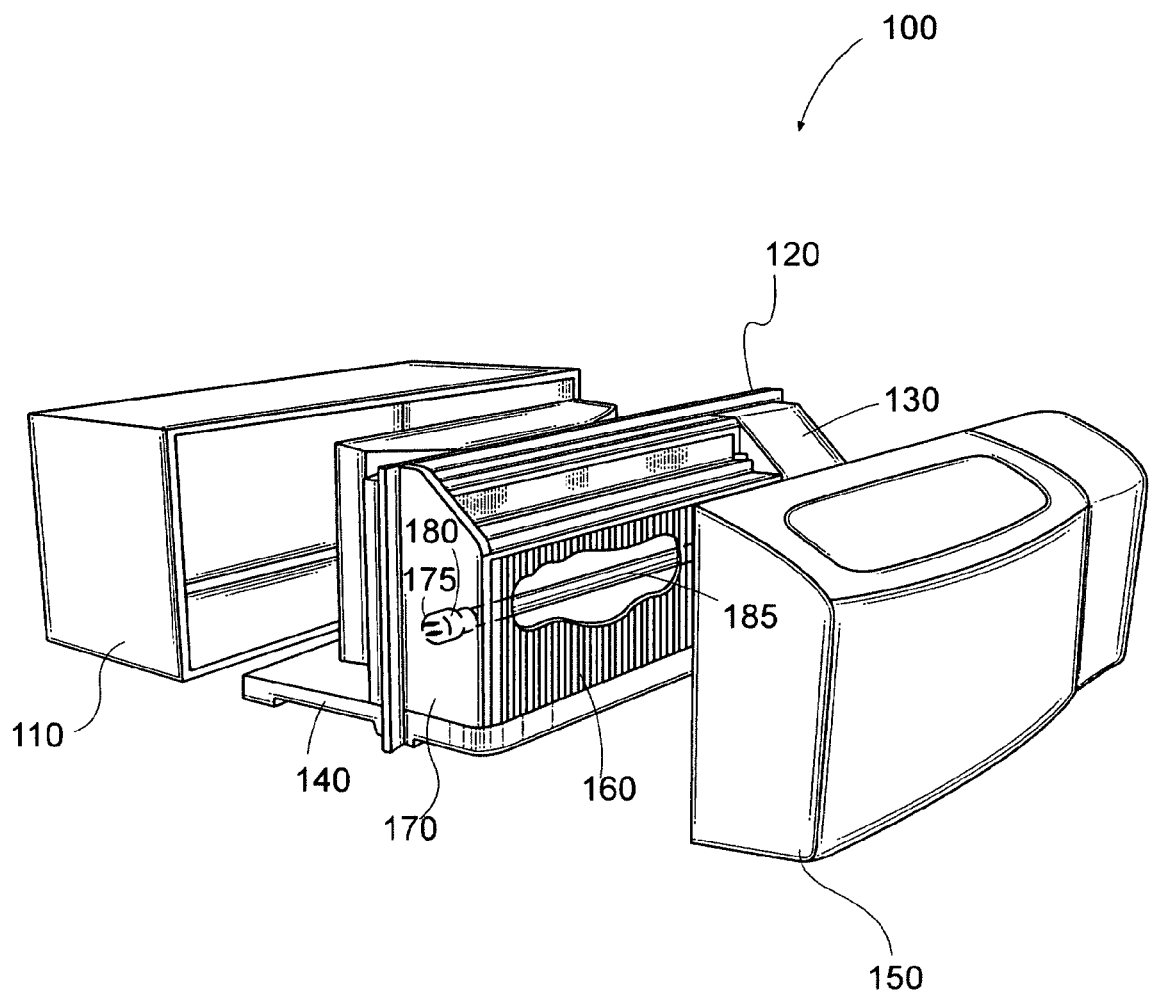
FIG. 1 is an exploded plan view of a PTAC.

Referring now to FIG. 1, there is shown an exploded plan view of a package terminal air conditioner (PTAC) 100. A PTAC is a single-package, through-the wall unit for heating and cooling rooms such as hotel rooms, school rooms, offices, apartments, condominiums, residential additions, and other rooms. A PTAC is a type of air handler. An air handler is an air conditioner that may be installed in a room as a stand alone unit. Stand alone units are also known as duct free systems. Other stand alone room air conditioners include unit ventilators, in-window room air conditioners, in-wall room air conditioners, and duct free systems.

The PTAC 100 may include a sleeve 110, a chassis 120, a cover 150 and a coil 160. The sleeve 110 may be disposed at least partially within a wall or ceiling of a room. The sleeve 110 may house the chassis 120. The sleeve 110 may provide mechanical support to the chassis 120. A chassis is a frame to which working parts of the device are mounted. The working parts may include a filter, electrical controls, a thermostat, and a power supply The chassis 120 may include a front section 130 and a rear section 140. When the PTAC 100 is installed in a room, the rear section 140 may be disposed within the sleeve 110 and the front section 130 maybe disposed within the room.

The front section 130 may include a wall 170. The wall 170 may enclose the working parts of the PTAC 100. The wall 170 may be constructed of steel, aluminum, a composite, or other material. The wall 170 maybe rigid.

The coil 160 maybe disposed within the front section 130. The coil 160 maybe a heat exchanger, such as a condenser. During normal operation of the PTAC 100, it is common for water to condense on the outer surfaces of a coil 160. The presence of water typically promotes accumulation and growth of undesirable substances. Undesirable substances may include at least one of mold, bacteria, fungi, viruses, mildew, allergens, spores, yeasts, mycotoxins, and endotoxins.

The efficiency of the PTAC 100 is related to the surface area of the coil 160. If there is accumulation of undesirable substances on the coil 160, the surface area of the coil 160 will be effectively reduced. If the surface area of the coil 160 is reduced, the PTAC 100 will run inefficiently and be more expensive to operate. Therefore, if buildup of undesirable substances is reduced or minimized, the PTAC 100 will run more efficiently and consume less energy during normal operation.

The indoor air quality of room in which the PTAC 100 operates is related to the accumulation of undesirable substances on the coil 160. A fan (not shown) of the PTAC 100 may move air past the coil 160 into the room. Because the air may pass over the coil 160, the undesirable substances may become airborne in the room. Thus, hotel guests, students, office employees, and residents may become ill more frequently. Health is a factor for employee and student performance. More frequent illness results in increased medical costs for individuals. Therefore, if accumulation of undesirable substances on the coil 160 is reduced or minimized, employee and student performance may be improved, and health care costs may be saved.

The cover 150 may conceal the chassis 120. When the cover 150 conceals the chassis 120, an individual may not touch the components of the chassis 120. The cover 150 may provide protection from mechanical components such as rotating fan blades. The cover 150 may provide protection from electrical components that may cause an electric shock. The cover 150 may be utilized for aesthetic purposes as the chassis 120 may not match the decor of the room or be pleasing to the eye.

The cover 150 may attach to the front section 130, the sleeve 110, or other part of the chassis 120. Because hotel rooms, school rooms, offices, apartments, condominiums, and residential additions are typically small in size, the PTAC 100 may be designed for space efficiency. In order to minimize space, the cover 150 may have dimensions that are slightly larger and similar in geometry to the front section 130. When the cover 150 is installed, there may be a maximum of approximately 1" of clearance between the wall 170 and the cover 150.

An electric discharge device 185 may be installed in the PTAC 100 or other air handler. The electric discharge device 185 may be an option, an upgrade, or a retrofit to a standard PTAC 100. The electric discharge device may include a tube 190. The term electric discharge device refers to an apparatus which emits radiation caused by an electric discharge from electrodes in a tube. An electric discharge is electrical conduction through a gas or vapor in an applied electric field. A tube is a hollow device used to hold vaporizable materials and gases. A tube may be at least partially translucent. A tube may be constructed of glass, metal, or plastic. Electric discharge devices may be fluorescent lamps, mercury vapor lamps, low pressure sodium lamps and high pressure sodium lamps.

The electric discharge device 185 may include a vaporizable material, such as mercury. The mercury, when electrically excited, may emit ultraviolet light at a germicidal wavelength. A germicidal wavelength may be at an ultraviolet-C (UVC) wavelength. A germicidal wavelength, for example 187 nm and 254 nm, is a wavelength of light which retards buildup or accumulation of undesirable substances.

The wall 170 may include an opening 175. The opening 175 may be the location in the wall 170 through which the electric discharge device 185 is installed. The location of the opening 175 may be selected so the electric discharge device 185 emits germicidal radiation to the coil 160. When installed, the electric discharge device 185 may be disposed within the front section 130.

When the electric discharge device 185 is installed, the electric discharge device may receive mechanical support from a mount 180. The mount 180 may be attached to the wall 170 at the opening 175. The opening 175 may have the shape of a circle, square, or other regular or irregular shape. The dimensions of the opening 175 may be selected based on the dimensions of the electric discharge device 185 and the mount 180. The opening 175 may have a diameter of approximately 1.25" or other dimension. The opening 175 may be preformed in the wall 170 during manufacturing of the PTAC 100. The opening 175 may be cut or punched out as a retrofit or upgrade to the PTAC 100.

The tube 190 may emit germicidal radiation in an air duct (not shown) to condition air that enters the room. This may at least partially sterilize the air that enters the room. The tube 190 may emit germicidal radiation on a fan (not shown) which moves air past the coil 160 and into the room. The tube 190 may emit germicidal radiation to a drain pan (not shown). The electric discharge device 185 may reduce or prevent accumulation of the undesirable substances on at least one of the coil 160, the air duct (not shown), the fan (not shown), and the drain pan.

Figure 2:
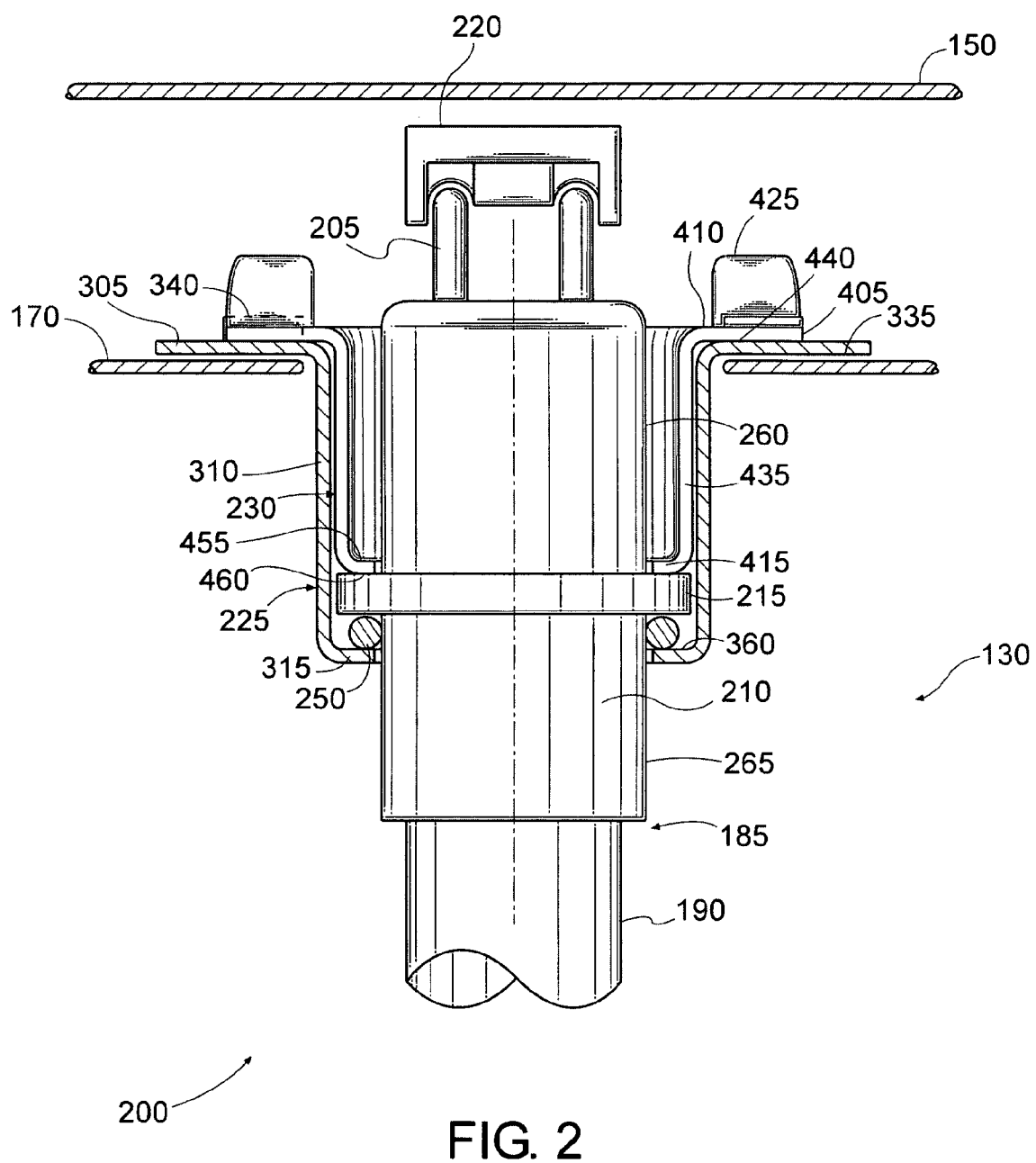
FIG. 2 is a cut-away perspective view of a mounting system.

Referring now to FIG. 2, there is shown a cut-away perspective view of a recessed mounting system 200. The recessed mounting system 200 includes a cradle 225, a retainer 230, an electric discharge device 185, and a wall 170. [FIX DRAWING 255-225 FIG. 2]

The electric discharge device 185 may include an electrical contact 205 and a stem 210. The stem 210 may include a rim 215, a first section 260, and a second section 265. The second section 265 of the stem 210 may attach to an end of the tube 190. The stem 210 may have the geometry of a cylinder or other shape. For example, the dimensions of the stem 210 may include a diameter of approximately 0.75", and a length of 1.25" or other dimensions.

A rim is a projecting edge or border. The rim 215 may be a mounting surface for the electric discharge device 185. The electric discharge device 185 may receive mechanical support at the rim. For example, the rim 215 may be secured by the mount 180. The rim 215 may be integral to the first section 260 and the second section 265. The rim 215 may extend radially, approximately ⅛" or other dimension, from a circumference of the stem 215. The rim 215 may have a diameter of approximately 1" or other dimension. The rim 215 may be coated with a ferrous or magnetic material. A magnet (not shown) may be attached to the rim 215 with an adhesive such as glue or double sided tape.

The electrical contact 205 may receive power from a socket 220. The electrical contact 205 may be attached to and/or embedded within the first section 260 of the stem 215. The electrical contact 205 may have an industry standard form such as a bi-pin, a single pin, a R17d, a medium bi-pin, a four pin, a 2Gx13, a recessed double contact, a G-23, or a 2G-11.

The socket 220 may be electrically connected to a power supply (not shown) via wiring (not shown). The power supply (not shown) may provide power to the electric discharge device 185 via the wiring, (not shown), and the socket 220. When electric power is provided to the electric contact 205, the electric discharge device 185 may emit radiation.

Figure 3:
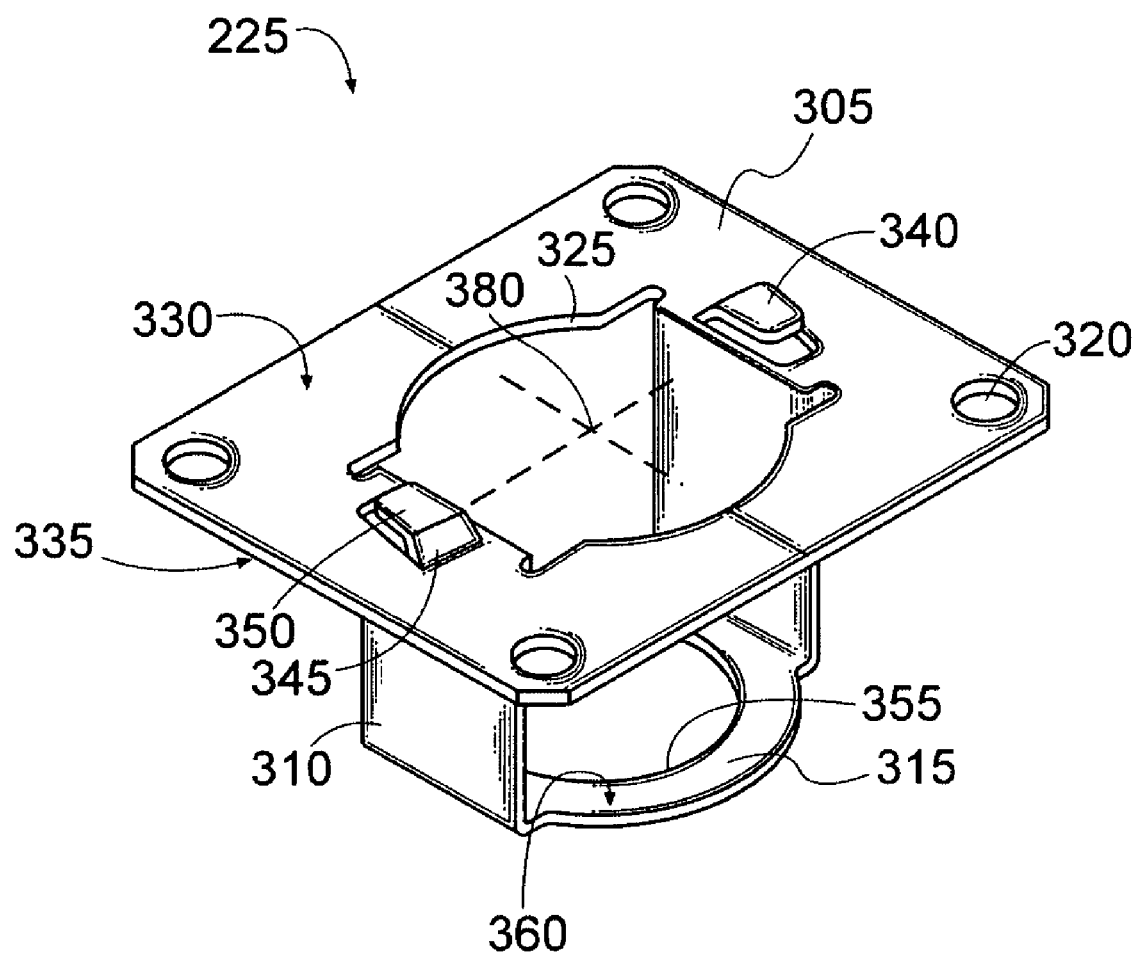
FIG. 3 is a plan view of a cradle.

The cradle 225, also shown in the plan view of FIG. 3, may include a flange 305, a cantilever 310, and a base 315. The cradle 225 may attach to the wall 170. The cradle 225 may be at least partially recessed within the chassis 170. The cradle 225 may provide mechanical support to the electric discharge device 185. The cradle 225 may at least partially recess the electric discharge device 185 within the chassis 225.

The cradle 225 may be machined and/or formed from a metal, injection molded with a plastic, or manufactured via another process. The cradle 225 may be constructed of a single piece of material. For example purposes, the cradle 225 may be manufactured from galvanized steel, polypropylene, carbon fiber, or other material. The cradle 225 may be coated with a urethane or other material. The coating (not shown) may protect the cradle 225 from corroding and insulate the cradle 225 from electric current.

Figure 5:
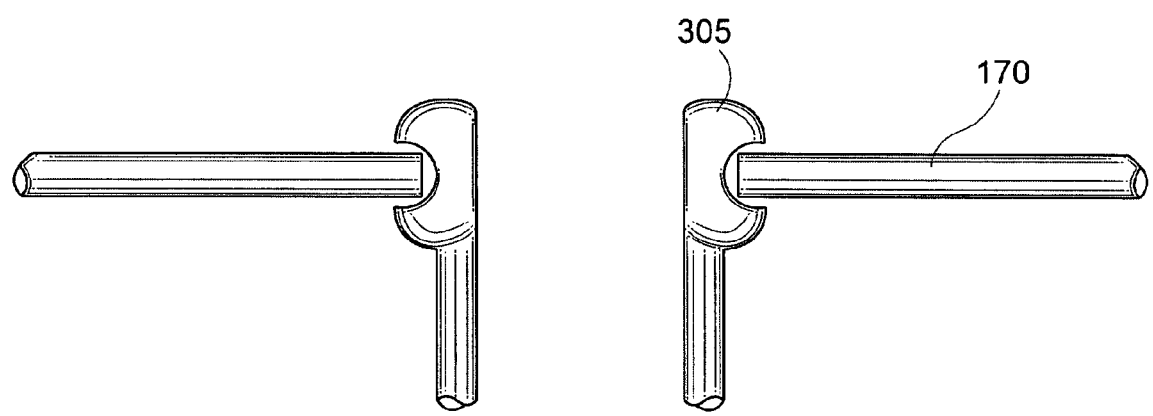
FIG. 5 is a partial cut-away perspective view of a cradle.
Figure 6:
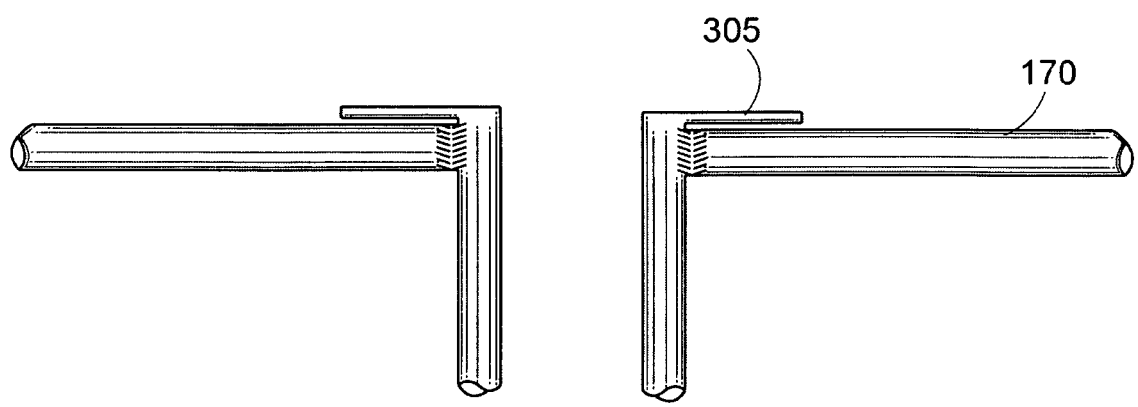
FIG. 6 is a partial cut-away perspective view of a cradle.

The flange 305 may include a first opening 320, a second opening 325, a top surface 330, a bottom surface 335, and an ear 340. A flange is a surface for attaching one body to another. The cradle 225 may be attached to the wall 170 via the flange 305. The flange 305 may be attached to the wall via a fastener, an adhesive, a magnet, or a welding. The flange 305 may be formed as a sleeve or channel, as shown in the partial cut-away perspective view of FIG. 5, which forms a friction fit or a snap fit between the flange 305 and the wall. The flange 305 may include threaded edges to screw into the wall 170, as shown in the partial cut-away perspective view of FIG. 6.

Referring again to FIG. 2, the flange 305 may have the geometry of a rectangle, square, circle, or other shape. For example purposes, the flange 305 may have dimensions of 1.4" in width, 1.7" in length, and 0.03" in thickness. The flange 305 may have rounded corners and beveled edges. Rounded corners and beveled edges may prevent installers from cutting their fingers during installation.

The first opening 320 may be a hole for a fastener (not shown) to pass through. The first opening 320 may be have a circular, square, or other shape. For example purposes, the first opening 320 may be a circular hole with a ⅛" diameter. Moreover, the flange 305 may include a plurality of second openings 325. The first opening 320 may be located near an edge of the flange 305 to provide for mounting stability. For example, the first opening 320 may be located at approximately 0.17" from an edge of the flange 305. The flange 305 may include a first opening 320 or a plurality of second openings 325.

When the flange 325 is attached to the wall 170, the bottom surface 335 may contact the wall 170. A gasket (not shown) may be disposed between the bottom surface 335 and the wall 170. The gasket may provide for a more secure fit, may prevent scratches between the bottom surface 335 and the wall 170, the gasket may reduce vibrations and/or shock from being transmitted from the chassis 120 to the electric discharge device 185.

Vibration refers to a periodic motion of a mass in alternately opposite directions from the position of equilibrium when that equilibrium has been disturbed, for example by a sinusoidal force. Vibration may occur when a compressor and/or a fan of an air handler is running. Shock refers to an impact as in a striking, an impinging, or a collision. Shock may occur when a person bumps into an air handler. Vibration and/or shock, if transmitted to the electric discharge device 185, may cause the tube 190 to prematurely fracture and/or fail. Installation of a gasket may reduce the frequency of replacement of the electric discharge device 185.

The second opening 325 may allow the electric discharge device 185 to pass through for installation. The second opening 325 may have a geometry that is circular, irregular or other shape. The dimensions of the second opening 325 may be selected to be larger in diameter than the circumferences of the tube 190, the stem 210, and the rim 215. For example, the second opening 325 may have a diameter of 1", or other dimension. The second opening 325 may be located near the center 380 of the flange 305. The second opening 325 may be offset from the center 380 of the flange 305.

The ear 340 may be a small tab which projects above the top surface 330 of the flange 305 to facilitate grasping of the retainer 230. The ear 340 may be bent in order to function as a catch. A catch is a device which clasps or seizes another device. The ear 340 may include a first section 345 integral to the flange 305. For example purposes, the ear 340 may be offset above the top surface 330 by approximately 0.04" or other dimension. The first section 345 may be disposed at an angle above the flange 305. The ear may include a second section 350. The second section may be integral to the first section 345. The second section 350 may be parallel to the top surface 330 of the flange 305. The second section 350 may be disposed at an angle of approximately 5 degrees or other angle relative to the top surface 330 of the flange 305. If the second section 350 tips up relative to the top surface 330 of the flange 305, the retainer 230 may engage the flange 225 more securely.

The ear 340 may include ribs (not shown) or clips (not shown). The ear 340 may include a magnetic coating. A magnet (not shown) may be attached to the ear 340. A rib, a clip, or a magnet may individually, or in combination, assist in securing the retainer 230 to the flange 305.

The cantilever 310 may offset the base 315 away from and in the direction the bottom surface 335 of the flange 305 faces. When the flange 305 is attached to the wall 170, the base 315 may be recessed within the chassis 120. A cantilever is a projecting member supported at only one end. The cantilever 310 may be integral with the flange 305 at the second opening 325 of the flange 305 or at another section of the flange 305. The cantilever 310 may have a cylindrical, a rectangular, or other geometry. The cradle 225 may include a cantilever 310 or a plurality of cantilevers 310. For example purposes, FIG. 3 shows two cantilevers 310.

The base 315 may be a mounting surface for securing the rim 215 of the electric discharge device 185. The base 315 may be supported by the cantilever 310. The base 315 may be integral with the cantilever 310. The base 315 may have the geometry of a circle, a rectangle, or other regular or irregular shape. For example purposes, the base 315 of FIG. 3 has a circular geometry with a diameter of approximately 1.12".

The base 315 may include an opening 355 and a top surface 360. The opening 355 may be circular or other geometry. The dimensions of the opening 355 may be selected to be larger than a circumference of the tube 190 of the electric discharge device 185, the second section 265 of the electric discharge device 185, but not the rim 215 of the electric discharge device 185. For example, the opening 355 may have a diameter of approximately 0.8". The tube 185 and the second section 265 of the electric discharge device 185 may pass through the opening 355 for installation.

The base 315 may include a ferrous coating. A magnet (not shown) may be attached to the base 315. A hook and loop fastener may be attached to the base 315 and the rim 215. A reusable or permanent adhesive may be applied to the base 315 and the rim 215. The rim 215 may be at least partially secured to the base 315 by one of or combinations of the magnet, the hook and loop fastener, and the adhesive.

The base 315 may be parallel to the flange 305. The base 315 may be normal to the cantilever 310. The term normal refers to perpendicular.

As shown in FIG. 2, when the electric discharge device 185 is installed in the mount 180, the rim 215 may be in contact with the top surface 360 of the base 315. A gasket 250 may be disposed between the rim 215 and the top surface 360 of the base 315. The gasket 250 may be an o-ring. The gasket may be constructed of a butyl rubber, a siliceous ring, or other material. The gasket 250 may provide for a more secure mounting of the electric discharge device 185. The gasket 250 may reduce the transmission of vibration and/or shock from the chassis 120 to the electric discharge device 185.

Figure 4:
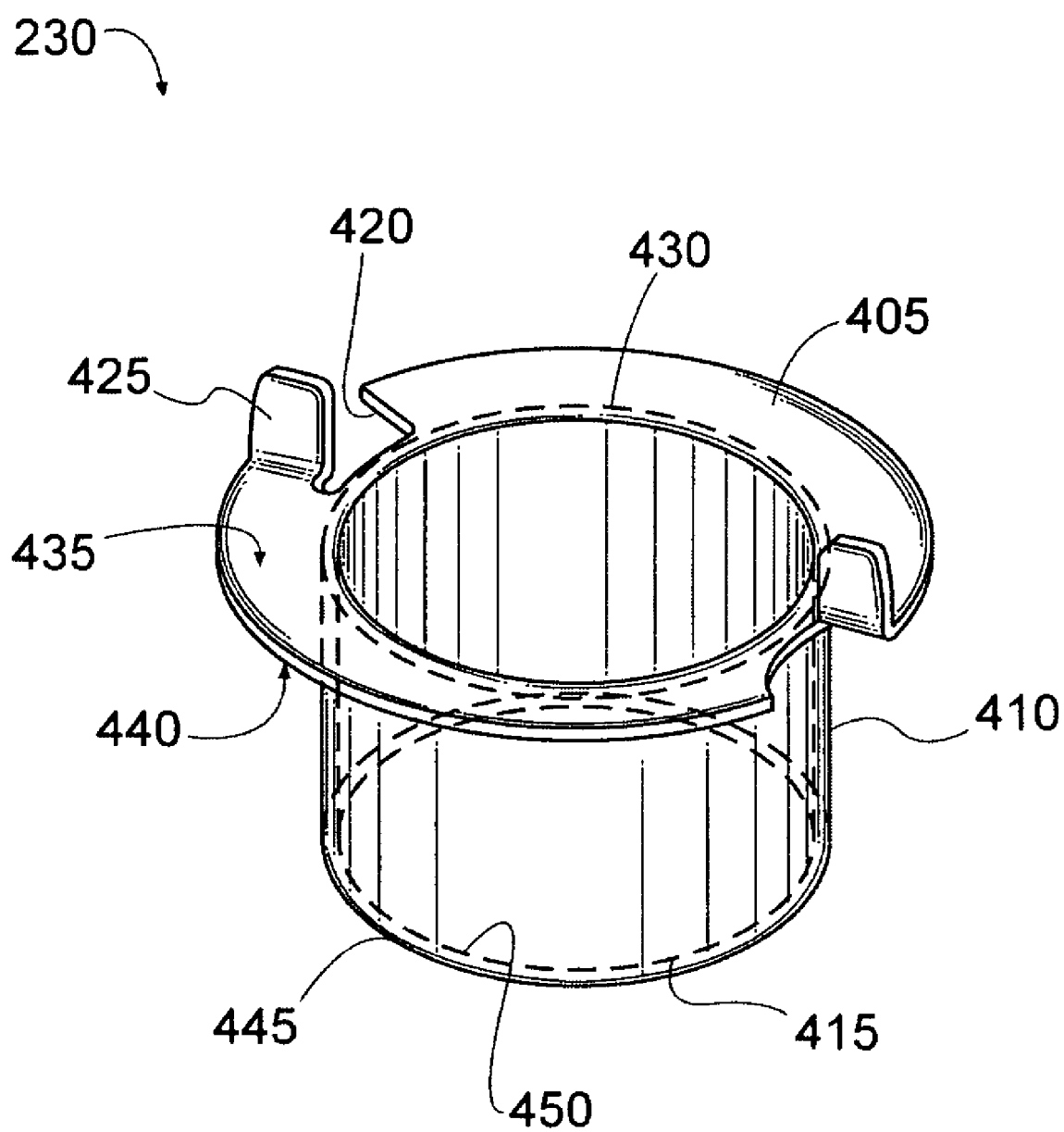
FIG. 4 is a plan view of a retainer.

The retainer 230, also shown in the plan view of FIG. 4, may engage the cradle 225 and secure the rim 215 to the base 315. A retainer is a device to hold another device in place. The retainer 230 may include a collar 405, a shaft 410, and a ring 415. The retainer 230 may be machined, molded, extruded or constructed via another process. The retainer 230 may include a coating (not shown) to protect from corrosion and insulate from electric current. For example purposes, the retainer 230 may be manufactured from galvanized steel, polypropylene, or carbon fiber.

The retainer 230 may engage the cradle 225 as a bayonet mount. The collar 405 may engage the flange 305 causing the retainer 230 to mate to the cradle 225. The collar 405 may include a top surface 410, a bottom surface 440, an edge 420, a tab 425, and an opening 430. The collar 430 may have the geometry of a circle, or other shape. For example purposes, the collar may have a diameter of 1.4". The collar may include an opening 430. The opening 430 may have the geometry of a circle, or other shape. The dimensions of the opening 430 may be selected to be larger than a circumference of the first section 260 of the stem 210. For example, the opening 430 may have a diameter of approximately 1". During installation, the opening 430 of the retainer 230 may pass over the first section 260 of the stem 210.

The tab 425 may be a handling member for an installer of the retainer 230. The tab 425 may be cut out from the collar

405. The tab 425 may be bent up from the collar 405. The tab 425 may be bent in the direction which the top surface 410 faces or another direction. For example, the tab 425 may have a length of approximately 0.3" and a width of approximately 0.25". The tab 425 may allow an installer of the mount 180 to rotate the retainer 230 when the retainer 230 is recessed within the cradle 225.

The top surface 410 of the collar 405 may include a rough surface (not shown). The rough surface may provide sufficient friction for an installer to rotate the retainer 230 with their fingertips. The top surface 410 of the collar 405 may include ridges (not shown). The ridges may provide a surface for the installer to rotate the retainer 230. The collar 405 may include a finger hole (not shown) or a series of finger holes. A finger hole is an opening through which the tip of a finger may fit. The finger hole may have a diameter of approximately 0.5". An installer may insert a finger into the finger hole to handle the retainer 230. The rough surface, the ridges, or the finger hole may be used individually, in combination with, or in lieu of the tab 425 to provide the installer with handling surfaces.

The edge 420 may be a section of the collar 405 from where the tab 425 was cut out from. The edge 420 may be bent slightly downward in the direction that the bottom surface 440 faces. When the retainer 230 is installed, the bottom surface 440 of the collar 405 may abut the top surface 330 of the flange 305. The retainer 230 may be rotated such that the edge 420 may slide under at least part of the ear 340. The edge 420 may engage the ear 340 via a friction fit. The edge 420 may engage the ear 340 via a latch, clasp, magnet, or other.

The shaft 435 may offset the ring 415 in the direction that the bottom surface 440 of the collar 405 faces. A shaft is an elongate hollow member, typically having the geometry of a cylinder. The shaft 435 may be integral with the collar 405. The shaft 435 may have the geometry of hollow cylinder or other geometry. In lieu of an elongate hollow member, the shaft 435 may be a cantilever or a plurality of cantilevers. The shaft 435 may be perpendicular to the collar 405. The dimensions of the shaft 435 may be selected to be larger than the first section 260 of the stem 210. For example purposes, the shaft may have a diameter of approximately 1" and a length of approximately 0.9". By offsetting the ring 415, when the retainer 230 is installed, the ring 415 may be recessed within the chassis 120.

A ring is a circular or curved band used for holding, pressing, or connecting. When the retainer 230 is engaging the cradle 225, the ring 415 may hold the rim 215 to the base 315. The ring 415 may have an outer edge 445, an inner edge 450, a top surface 455, and a bottom surface 460. The ring 415 may be perpendicular to the shaft 435. The ring 415 may be parallel to the collar 405. The shaft 435 may be integral with the outer edge 445 or another portion of the top surface 455.

The dimensions of the outer edge 445 may be selected to be smaller than the opening 320 of the flange 305. The geometry of the outer edge 445 may be circular or another shape. For example purposes, the outer edge 445 may have a diameter of approximately 1" or other. The dimensions of the inner edge 450 may be selected to be both larger than the circumference of the stem 210 and smaller than the circumference of the rim 215. The geometry of the inner edge 450 may be circular or another shape. For example purposes, the inner edge 450 may have a diameter of approximately 0.79" or other.

The inner edge 450 may define an opening. During installation, the inner edge 450 may pass around the electrical contact 205 and the first section 260 of the electric discharge device 185. During installation, the bottom surface 460 of the ring 415 may contact the rim 215. When the retainer 230 engages the cradle 225, the bottom surface 460 of the ring 415 may press the rim 215 against the top surface 360 of the base 315.

Figure 7:
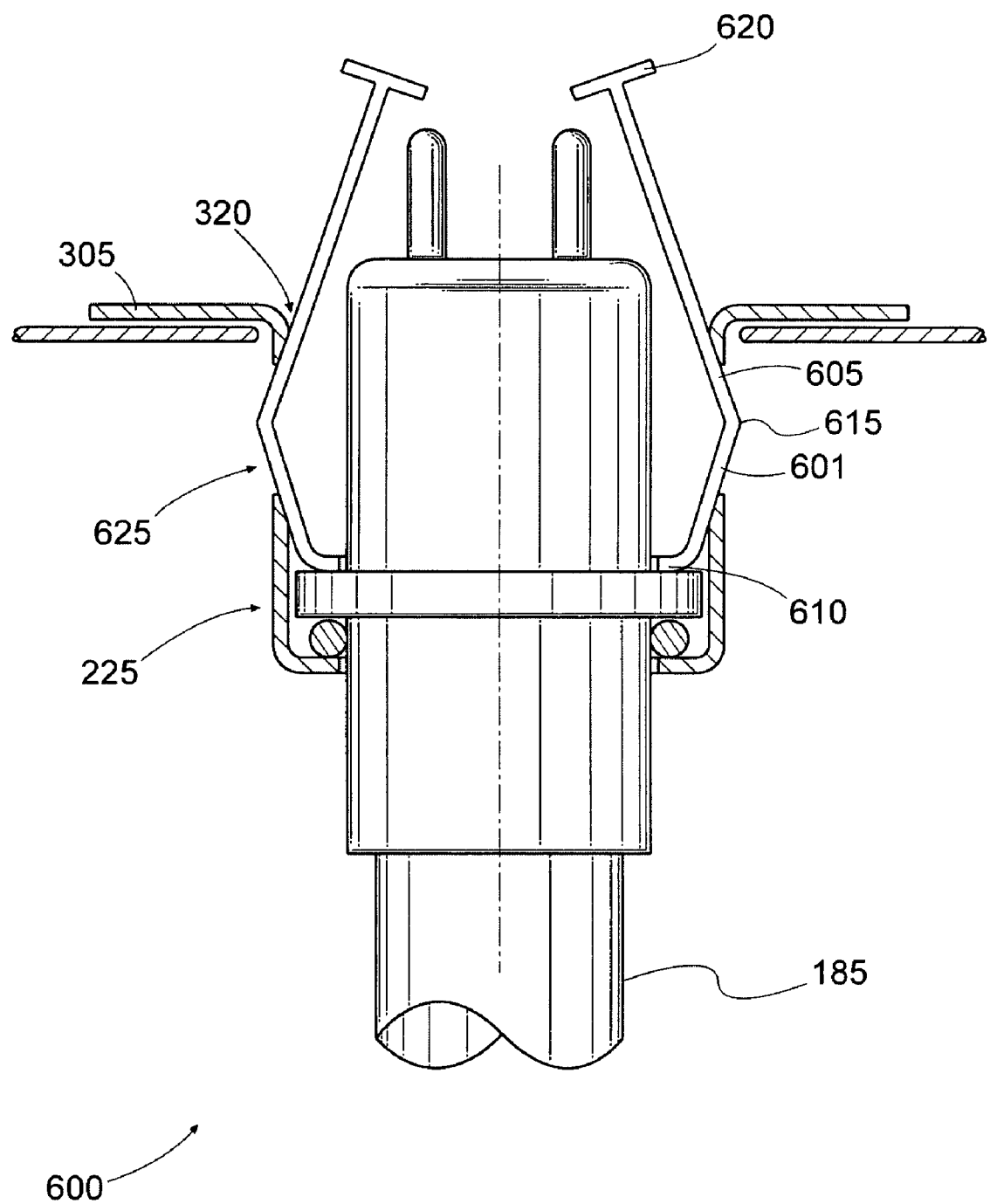
FIG. 7 is a cut-away perspective view of a mounting system.

Referring now to FIG. 7, there is shown a cut-away perspective view of a mounting system 600. The mounting system 600 may include a wall 170, a cradle 225, a retainer 601, and an electric discharge device 185. The retainer 601 may include a cantilever 605 and a ring 610. The cantilever 605 may be integral to the ring 610. The cantilever 605 may include a bend 615 and tab 620. The tab 620 may function as a handling member. When the ring 610 is inserted through the second opening 325 of the flange 305, the bend 615 may engage a slit 625 of the cantilever 310 of the cradle 225. Alternatively, the cantilever 605 of the retainer 601 may form a friction fit with the cantilever 310 of the cradle 225. The cantilever 605 may be flexible such that an installer may squeeze the tab 620 to disengage the bend 615 from the cantilever 310 of the cradle 225.

Referring again to FIG. 2, the electric discharge device 185 may be assembled with an air handler based on the following process steps:

(1) An opening 175 may be created in a wall 170 of a chassis of an air handler;

(2) A base 315 of a cradle 225 may be inserted through the opening 175 into the chassis;

(3) A flange 305 of the cradle 225 may be secured to the wall 170, thereby recessing the base 315 in the chassis;

(4) A tube 190 of an electric discharge device 185 may be inserted through an opening 355 of the base 315 into the chassis;

(5) A ring 415 of a retainer 230 may be inserted into the cradle 225 around an electrical contact 205 and a first section 260 of a stem 210 of the electric discharge device 185;

(6) The retainer 230 may engage the cradle 225 causing the ring 415 to press a rim 215 of the electric discharge device 185 against the base 315.

The electric discharge device 185 may be periodically replaced, for example, at the end of its life cycle. Because the retainer 230 may be easily disengaged from the cradle 225, the electric discharge device 185 may be removed from the chassis 120 and replaced without taking apart the chassis 120. Because the chassis 120 need not be taken apart, maintenance costs may be saved.

When the electric discharge device 185 is installed in the air handler, the electric discharge device 180 may be at least partially recessed within the chassis 120. When the electric discharge device 185 is recessed within the front section 130, the electrical contact 205 may protrude no more than ½" in length outside of the wall 170. When the electric discharge device 185 is recessed within the front section 130, the socket 220 may protrude no more than ¾" in length outside of the wall 170. Because the cradle 225 and retainer 230 may recess the electric discharge device 185 at least partially within the front section 130, the electrical contact 205, the socket 220 and the wiring (not shown) will not interfere with the cover 150.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications and alterations should therefore be seen as within the scope of the present invention.

The invention claimed is:

1. A recessed cantilever mount comprising:
   a chassis comprising a wall, the wall comprising an opening;
   a cradle adapted to attach to the wall and extend through the opening into the chassis;
   an electric discharge device comprising a stem and a tube;
   a retainer adapted to attach to the cradle and secure the stem to the cradle, wherein the stem is at least partially recessed in the cradle, and the tube is recessed within the chassis.

2. The recessed cantilever mount of claim 1, wherein an electrical contact of the stem extends less than about ½ inch outside the wall when the stem is secured to the cradle.

3. The recessed cantilever mount of claim 2, wherein the retainer is adapted to attach to the cradle with a bayonet mount.

4. The recessed cantilever mount of claim 1, wherein the tube emits germicidal radiation.

5. The recessed cantilever mount of claim 4, wherein the chassis further comprises a condenser coil, wherein the tube emits germicidal radiation to the condenser coil.

6. The recessed cantilever mount of claim 5, wherein a socket connected to the electric discharge device extends less than about ¾ outside the wall.

7. The recessed cantilever mount of claim 6, further comprising a first gasket disposed between the stem and the cradle.

8. The recessed cantilever mount of claim 7, further comprising a second gasket disposed between the stem and the retainer.

9. The recessed cantilever mount of claim 1, wherein the retainer is a magnet adapted to be disposed between the stem and the cradle.

10. The recessed cantilever mount of claim 1, wherein the chassis is a package terminal air conditioner chassis.

11. A recessed mount comprising:
    a cradle comprising a flange, a cantilever, and a base;
    the base offset below the flange via the cantilever;
    a retainer comprising a collar, a shaft, and a ring;
    the ring offset below the collar via the shaft;
    the flange adapted to secure to a wall;
    the ring adapted to secure a rim of a lamp to the base when the shaft is inserted through an opening of the flange and an edge of the collar is positioned below an ear of the flange.

12. The recessed mount of claim 11, wherein the flange comprises an opening adapted for the lamp to pass through for installation, and a top surface, the ear protruding above the top surface.

13. The recessed mount of claim 12, wherein the base comprises an opening adapted for a tube of the lamp to pass through for installation, the base is normal to the cantilever and parallel to the flange.

14. The recessed mount of claim 13, wherein the ring is normal to the shaft and parallel to the collar.

15. The recessed mount of claim 14, wherein an electrical contact of the lamp extends less than about ½ inch outside the wall when the stem is secured to the cradle.

16. The recessed mount of claim 15, wherein the edge attaches to the flange as a bayonet mount.

17. The recessed mount of claim 16, wherein the lamp emits ultraviolet-C radiation.

18. The recessed mount of claim 17, wherein the lamp emits ultraviolet-C radiation to a condenser coil.

19. The recessed mount of claim 18, wherein the wall is a package terminal air conditioner chassis wall.

20. The recessed mount of claim 18, wherein the wall is a unit ventilator wall.

21. The recessed mount of claim 19, wherein a socket connected to the electrical contact extends less than about ¾ outside the wall.

22. The recessed mount of claim 21, further comprising a first gasket disposed between the rim and the base.

23. The recessed mount of claim 22, further comprising a second gasket disposed between the rim and the ring.

24. The recessed mount of claim 11, wherein:
    the wall is a wall of an air handler chassis,
    the lamp is an electric discharge device, the lamp further comprising an electrical contact;
    the cradle is a single piece cradle;
    the flange is attached to the wall;
    the base is recessed in the air handler chassis;
    the retainer is a single piece retainer;
    the collar engages the flange;
    at least part of the electrical contact is recessed in the air handler chassis.

25. The recessed mount of claim 24, wherein the lamp is a germicidal lamp.

26. The recessed mount of claim 25, wherein the base may pass through the opening for installation.

27. The recessed mount of claim 26, wherein the lamp may pass through the opening for installation.

28. The recessed mount of claim 27, wherein the base comprises an opening through which a tube of the lamp may pass through for installation.

29. The recessed mount of claim 28, wherein the ring is normal to the shaft and parallel to the collar.

30. The recessed mount of claim 29, wherein the electrical contact extends less than about ½ inch outside the wall when the rim is secured to the base.

31. The recessed mount of claim 30, wherein the collar attaches to the flange as a bayonet mount.

32. The recessed mount of claim 31, wherein the tube emits germicidal radiation to a condenser coil.

33. The recessed mount of claim 32, wherein a socket connected to the electrical contact extends less than about ¾ outside the wall.

34. The recessed mount of claim 33, further comprising a first gasket disposed between the rim and the base.

35. The recessed mount of claim 34, further comprising a second gasket disposed between the rim and the ring.

36. A process for installing a germicidal system comprising:
    creating an opening in a wall of a chassis of an air handler selected from the group comprising a package terminal air conditioner and a unit ventilator;
    inserting a base of a cradle through the opening into the chassis;
    securing a flange of the cradle to the wall;
    inserting a tube of an electric discharge device through an opening of the base into the chassis;
    inserting a retainer into the cradle;
    pressing a ring of the retainer against a rim of the electric discharge device to position the rim against the base;
    engaging the retainer and the cradle to secure a collar of the retainer to the flange.

37. The process for installing a germicidal system of claim 36, wherein positioning the rim against the base positions the tube to emit radiation to a condenser coil.

38. The process for installing a germicidal system of claim 37, wherein the collar is secured to the flange as a bayonet mount.

39. A process for installing a germicidal system comprising:
   recessing a base of a cradle through an opening in a wall of a chassis of an air handler selected from the group comprising a package terminal air conditioner and a unit ventilator;
   securing the cradle to the wall;
   inserting a tube of an electric discharge device through an opening of the base into the chassis;
   securing a rim of the electric discharge device against the base.

40. The process for installing a germicidal system of claim 39, wherein the rim is secured against the base magnetically.

41. The process for installing a germicidal system of claim 40, wherein the rim is secured against the base with a retainer.

42. The process for installing a germicidal system of claim 40, wherein securing the rim against the base positions the tube to emit radiation to a condenser coil.

* * * * *